(12) United States Patent
Yevmenenko et al.

(10) Patent No.: US 10,307,547 B2
(45) Date of Patent: Jun. 4, 2019

(54) THUMB PRESS FRANGIBLE FEATURE FOR RE-USE PREVENTION

(71) Applicant: Becton, Dickinson and Company, Franklin Lakes, NJ (US)

(72) Inventors: Yan Yevmenenko, New York, NY (US); Andrew Wong, East Hanover, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 14/306,343

(22) Filed: Jun. 17, 2014

(65) Prior Publication Data

US 2014/0296781 A1    Oct. 2, 2014

Related U.S. Application Data

(63) Continuation of application No. 13/693,163, filed on Dec. 4, 2012, now Pat. No. 8,784,376.

(51) Int. Cl.
*A61M 5/50* (2006.01)

(52) U.S. Cl.
CPC .......... *A61M 5/5066* (2013.01); *A61M 5/502* (2013.01); *A61M 2005/5073* (2013.01)

(58) Field of Classification Search
CPC ............... A61M 5/5066; A61M 5/502; A61M 5/31501; A61M 2005/5073; A61M 5/5013; A61M 5/504; A61M 5/5086
USPC ........................................................ 604/110
See application file for complete search history.

(56) References Cited

U.S. PATENT DOCUMENTS

| | | | |
|---|---|---|---|
| 4,932,941 A | 6/1990 | Min et al. | |
| 5,000,736 A | 3/1991 | Kaufhold, Jr. et al. | |
| 5,106,372 A | 4/1992 | Ranford | |
| 5,114,404 A * | 5/1992 | Paxton .................. | A61M 5/315 604/110 |

(Continued)

FOREIGN PATENT DOCUMENTS

| | | |
|---|---|---|
| CN | 100423798 | 10/2008 |
| EP | 2928529 A1 | 10/2015 |

(Continued)

OTHER PUBLICATIONS

Non-Final Office Action in U.S. Appl. No. 13/693,163, dated Nov. 22, 2013, 11 pages.

(Continued)

*Primary Examiner* — Kevin C Sirmons
*Assistant Examiner* — Leah J Swanson
(74) *Attorney, Agent, or Firm* — Servilla Whitney LLC (57) ABSTRACT

Syringe assemblies having a passive disabling system to prevent reuse are provided. According to one or more embodiments, the syringe assembly comprises a barrel, plunger rod and detachable thumb press wherein the plunger rod further comprises flexible locking petals that lock the plunger rod within the barrel, a ramp disposed adjacent to the locking element, and one or more frangible connection or break point at the proximal end of the plunger rod disposed either inside the thumb press or immediately adjacent to the thumb press to separate the thumb press from the main body of the plunger rod when a user applies sufficient proximal force to the plunger rod after it has been locked within the barrel.

13 Claims, 10 Drawing Sheets

(56) References Cited

U.S. PATENT DOCUMENTS

| | | | |
|---|---|---|---|
| 5,304,138 A | 4/1994 | Mercado et al. | |
| 5,531,691 A | 7/1996 | Shonfeld et al. | |
| 6,632,198 B2 | 10/2003 | Caizza | |
| 8,784,376 B2* | 7/2014 | Yevmenenko | A61M 5/502 604/110 |
| 2004/0153037 A1 | 8/2004 | Huang | |
| 2004/0176722 A1 | 9/2004 | Capes et al. | |
| 2006/0052748 A1 | 3/2006 | Coelho et al. | |
| 2006/0211985 A1 | 9/2006 | Wang | |
| 2007/0049872 A1* | 3/2007 | Watts | A61M 5/31501 604/187 |
| 2008/0097305 A1 | 4/2008 | Tsai | |
| 2008/0154196 A1 | 6/2008 | Moh et al. | |
| 2009/0048560 A1 | 2/2009 | Caizza et al. | |
| 2009/0131869 A1 | 5/2009 | Caizza et al. | |
| 2010/0076378 A1 | 3/2010 | Runfola | |
| 2010/0268160 A1* | 10/2010 | Eccard | A61M 5/5066 604/110 |
| 2010/0286609 A1 | 11/2010 | Mahurkar | |
| 2011/0092903 A1 | 4/2011 | Caizza et al. | |
| 2014/0155826 A1 | 6/2014 | Yevmenenko | |

FOREIGN PATENT DOCUMENTS

| | | |
|---|---|---|
| JP | 2008504928 A | 2/2008 |
| WO | 2014/088993 A1 | 6/2014 |

OTHER PUBLICATIONS

PCT International Search Report and Written Opinion in PCT/US2013/072728, dated Feb. 25, 2014, 11 pages.
European Patent Office Communication in Appln. No. EP 13812282.5 dated Jul. 19, 2017, 4 pages.

* cited by examiner

THUMB PRESS FRANGIBLE FEATURE FOR RE-USE PREVENTION

CROSS-REFERENCE TO RELATED APPLICATIONS

This application is a continuation of U.S. patent application Ser. No. 13/693,163, filed on Dec. 4, 2012, the disclosure of which is incorporated herein by reference in its entirety.

TECHNICAL FIELD

Embodiments of the present invention relate to syringe assemblies having a passive locking mechanism which restricts distal/proximal movement of the plunger rod after injection to allow for detachment of the thumb press from the plunger to prevent reuse. The syringe assemblies may include a frangible element between the thumb press and plunger rod which allows the thumb press and plunger rod to be removably connected to prevent disassembly of the syringe during use and to allow disassembly after use.

BACKGROUND

Reuse of hypodermic syringe products without sterilization or sufficient sterilization is believed to facilitate the transfer of contagious diseases.

A syringe which can be rendered inoperable after use presents a viable solution to these issues. Various syringes have been proposed and are commercially available that can be disabled by the user by taking active steps to disable the syringe. Single-use syringes that do not require the user to actively disable the syringe are also thought to offer a solution.

Prior art re-use prevention syringes containing frangible features position the frangible section near the stopper end or near the middle of the plunger rod. This positioning makes the plunger rod prone to the accidental breakage in bending due to the substantial lever distance from the frangible break section to the point of force application at the thumb press, which results in user dissatisfaction and adds to health care costs by wasting the device and the medication it contains. The prior art frangible section location may also make the plunger rod substantially flexible, requiring the clinician to change their conventional technique.

Several prior art re-use prevention syringes attempt to improve their lack of rigidity by making the frangible feature a plurality of break points. This adds manufacturing complexity by requiring intricate tooling (such as interlocking thin molding inserts) that is difficult to produce and maintain, which results in increased product cost, and by challenging the plastic to flow through multiple narrow channels of the frangible section, which may result in molding defects.

The prior art multiple frangible points solution leads to inconsistent axial break forces due to the cumulative effect of the manufacturing tolerances on each individual break feature. The present invention of the single frangible element adjacent to the thumb press requires that only one critical feature be dimensionally controlled to ensure consistent axial break forces, thus further improving the product performance over the prior art.

It would be desirable to provide syringes that are automatically or passively disabled from reuse and can be manufactured in a cost-effective manner by, for example, utilizing fewer or less complex parts. It is also desirable to provide a re-use prevention syringe wherein the frangible features are reinforced or positioned to reduce to possibility of accidental breakage.

SUMMARY

A passive disabling system for a syringe assembly that activates after completion of an injection cycle is provided. A syringe assembly incorporates plunger rod with thumb press attached in a manner to prevent users from reusing or disassembling the syringe after completion of the injection cycle. In one or more embodiments of the invention, a user can fill, inject and/or reconstitute medication.

A syringe assembly is provided which includes a barrel, an elongate plunger rod with thumb press, and a locking element disposed on the barrel and/or plunger rod having respective structures and assembly which allow the user to passively lock the plunger rod within the barrel to prevent reuse of the syringe assembly. A frangible element is located between the thumb press and plunger rod which allows the thumb press and plunger rod to be removably connected to prevent disassembly of the syringe during use and to allow disassembly after use. In one or more embodiments, a ramp may be disposed proximally adjacent to the locking element having an increasing diameter from the locking element to the open proximal end. In one or more embodiments, the thumb press and plunger rod may be molded as one piece. The barrel includes a distal end, an open proximal end, a cylindrical sidewall with an interior surface, which defines a chamber in which fluid may be held, and a distal wall. An opening in the distal wall permits fluid to flow from the chamber through the opening. In one or more embodiments, the application of a continuous distally directed force to the plunger rod causes the stopper and plunger rod to move together in the distal direction within the barrel until the locking element locks the plunger rod in the barrel and a subsequent application of a proximally directed force to the plunger causes the frangible portion of the plunger rod to break and separates the thumb press from the main body of the plunger rod to prevent reuse of the syringe assembly.

In one or more embodiments, the interior surface of the sidewall, roof or floor of the barrel includes a tapered neck portion adjacent to the proximal end. In a specific embodiment, the tapered neck portion defines a second cross-sectional width that is less than the first cross-sectional width defined at the remaining portions of the interior surface. In another embodiment, the tapered neck portion defines a second cross-sectional width that is greater than the first cross-sectional width defined at the remaining portions of the interior surface. The tapered neck portion forms an impediment for restricting the proximal movement of the plunger rod.

Embodiments of the present invention also include a plunger rod which has a proximal end, a distal end, and a main body between the proximal and distal end. A thumb press is disposed at the proximal end of the plunger rod. In some embodiments, the plunger rod slides or otherwise moves proximally and distally within the chamber of the barrel.

The distal end of the plunger may include a stopper-engaging portion having a distal and proximal end. The plunger rod also may include a flexible locking petal or petals that are disposed between the thumb press and the main body of the plunger rod. The flexible locking petal of one or more embodiments includes a cross-sectional width that is greater than the second cross-sectional width or the cross-sectional width of the barrel at the tapered neck portion. In one or more alternative embodiments, the plunger rod may include a support member that includes an outer edge. The support member may be disposed proximally adjacent to the flexible locking petal. The flexible locking petal of one or more embodiments facilitates distal movement of the plunger rod by flexing in the proximal direction as a force is applied in the distal direction to the plunger rod. The plunger rod includes a frangible element that is disposed proximally adjacent to the thumb press. The frangible element may include two or more point connections disposed adjacent to the thumb press.

In one or more specific embodiments, the frangible element may include one or more point connections.

A syringe assembly of one or more embodiments may include a stopper including a proximal end and a distal end. The stopper may be attached to the stopper-engaging portion of the plunger rod such that as the stopper approaches the distal wall of the barrel, the flexible locking petals are permitted to advance distally past the tapered neck portion and lock the plunger rod in the barrel to prevent reuse of the syringe assembly.

In one or more embodiments, the application of a force in the distal direction to the plunger rod causes the stopper and the plunger rod to move together in the distal direction until the stopper reaches the distal end of the barrel, thereby allowing the locking petal to advance distally past the tapered neck portion in the barrel and lock the plunger rod in the barrel to prevent reuse of the syringe assembly. After the plunger rod has been locked in the barrel, the application of a proximally directed force to the plunger rod causes the frangible portion connecting the plunger rod and thumb press to break.

In one or more embodiments, the one or more point connections of the frangible element are adapted to withstand application of a force on the plunger rod in the distal direction and break upon application of a force in the proximal direction after the flexible locking petal has advanced distally past the tapered neck portion. In one or more embodiments, the force required to move the plunger rod in the proximal direction after the flexible locking petal has advanced distally past the tapered neck portion exceeds the force required to break the one or more point connections.

In one or more embodiments, the frangible element is disposed inside or under the thumb press and may have a single break point or plurality of break points inside or under the thumb press.

In one or more embodiments, the frangible element comprises a knock-out tab disposed inside the thumb press and extending radially from the thumb press to the plunger rod body. The knock-out tab may include four break points, each break point extending radially to removably attach the thumb press to the plunger rod body In one or more embodiments, the syringe assembly may further include a spacer clip disposed between the thumb press and plunger rod. The spacer clip may comprise one or more anti-rotation bumps and retaining hooks. In one or more embodiments, the spacer clip is formed from a wire.

In one or more embodiments, the syringe assembly may comprise a step molded into the plunger rod to accommodate the spacer clip and register the retaining hooks of the spacer clip.

In one or more embodiments, the spacer clip and frangible element are disposed at a distance from the thumb press.

In one or more embodiments, a spacer in the form of a protrusion or bump may be disposed between the thumb press and plunger rod to fill the gap around the frangible element located between the thumb press and plunger rod to restrict the range of motion about the frangible element.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

In this disclosure, a convention is followed wherein the distal end of the device is the end closest to a patient and the proximal end of the device is the end away from the patient and closest to a practitioner.

The present invention provides a frangible element adjacent to the thumb press to minimize the moment arm and thus optimizes the plunger rod bending strength and rigidity.

The improved stability of the present invention affords the implementation of a single frangible element comprising one or more break points under the thumb press, which due to its simple geometry, the present invention provides the ease of manufacture, cost, and quality advantages over the prior art syringes.

One aspect of the present invention provides for a syringe assembly including a barrel, plunger rod with thumb press, one or more locking elements, and stopper having individual features and construction which allow the user to passively lock the plunger rod within the barrel to prevent reuse of the syringe assembly. In one or more embodiments, the barrel may include one or more locking elements adjacent its proximal end or other means for locking the plunger rod within the barrel. In one or more embodiments of the present invention, the locking element may be in the form of a protrusion, notch, rib or tapered neck. In one or more embodiments, the inner diameter of the barrel at the location of the locking element or other locking means is smaller than the inner diameter of the barrel at other locations along the length of the barrel. In another embodiment, the inner diameter of the barrel at the location of the locking element or other locking means is greater than the inner diameter of the barrel at other locations along the length of the barrel. It will be understood that the locking element can have different shapes and configurations. A ramp may be disposed proximally adjacent to the locking element having an increasing diameter from the locking element to the open proximal end. An increased diameter region may be disposed proximally adjacent to the ramp. The present invention also provides a syringe assembly including a removably connected thumb press and plunger rod to prevent disassembly of the syringe during use and to allow disassembly after use.

In one or more embodiments of the present invention, the syringe assembly includes a single frangible element with a compliant thumb press. The single circular frangible element is shown adjacent to the thumb press. Due to the gap under the thumb press required to mold the frangible element, the thumb press has some compliance during normal use.

The present invention provides a re-use prevention feature of a syringe containing a frangible element that is located adjacent to or inside the plunger rod thumb press. When an attempt is made to re-use a locked re-use prevention syringe by pulling on the plunger rod thumb press, the frangible element breaks before the re-use prevention lock is disengaged, thus permanently disabling the syringe from further use. Placing the frangible element adjacent to the thumb press or inside the thumb press improves the plunger rod's bending strength and rigidity by minimizing the moment arm from the thumb press to the one or more break points of the frangible element.

Figure 1:
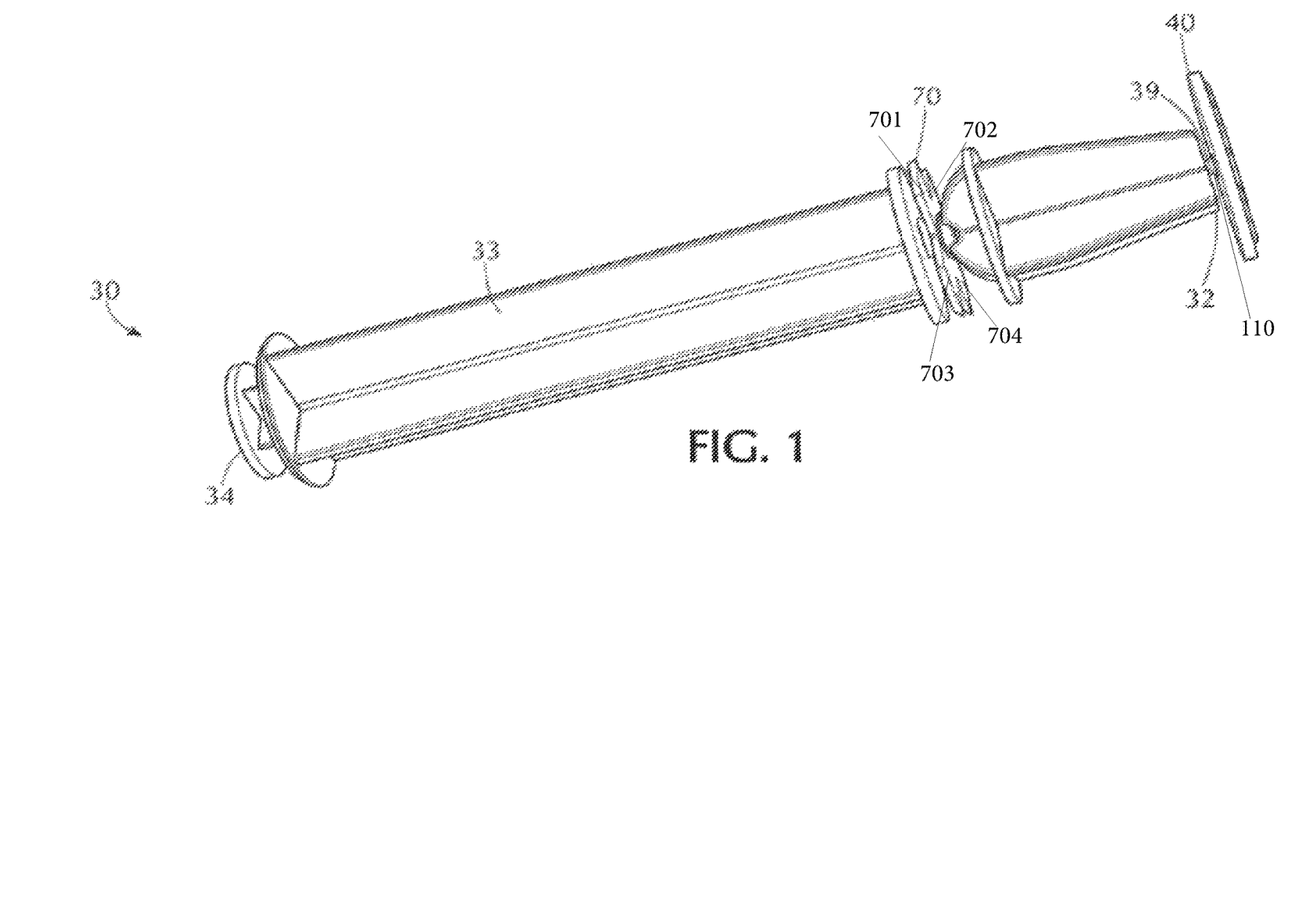
FIG. 1 shows a perspective view of a plunger rod and thumb press according to an embodiment of the invention showing a single frangible element disposed between the thumb press and plunger rod.

The present invention positions the frangible element adjacent to the plunger rod thumb press, minimizing the moment arm, to improve the plunger rod's bending strength and rigidity. The improved stability of such configuration allows the use of a single break point, which eliminates the manufacturing complexity, reduces the cost, and improves the product performance and quality of the prior art devices. FIG. 1 shows a plunger rod 30 according to one or more embodiments. Referring now to FIG. 1, the syringe assembly includes a plunger rod 30 having a proximal end 32, a distal end 34, and a main body 33 extending between the proximal end 32 and distal end 34. The plunger rod 30 further includes a thumb press 40 at the proximal end 32 of the plunger rod 30. In the embodiment shown, the thumb press 40 is connected to the plunger rod by a frangible element 39. FIG. 1 shows a perspective view of a plunger rod 30 and thumb press 40 according to an embodiment of the invention showing a single frangible element 39 disposed between the thumb press and plunger rod. The plunger rod body 33 shown in FIGS. 1-15 includes two transverse members which intersect to form a cross-shaped body that defines four quadrants between the two transverse members. The transverse members and the quadrants extend from the distal end 34 to the proximal end 32 of the plunger rod and are intersected by a flexible locking petals 70 and frangible element 39. The dimensions of the transverse members may vary along the length of the plunger rod body 33. For example, as shown in FIG. 1-5, the cross-sectional width of the transverse members decreases adjacent to the distal end of the thumb press 40, decreasing the cross-sectional width of the plunger rod body 33. In one or more embodiments, a stopper-engaging portion may be included on the distal end 34 of the plunger rod 30. In one embodiment of the invention, a press-fit attachment or other suitable means for retaining the end of the stopper may be included. In one or more embodiments, the stopper is integrally formed with the plunger rod. According to one or more embodiments, the stopper may be formed from an elastomeric or plastic material. The stopper may also be formed from other known materials in the art.

Figure 2:
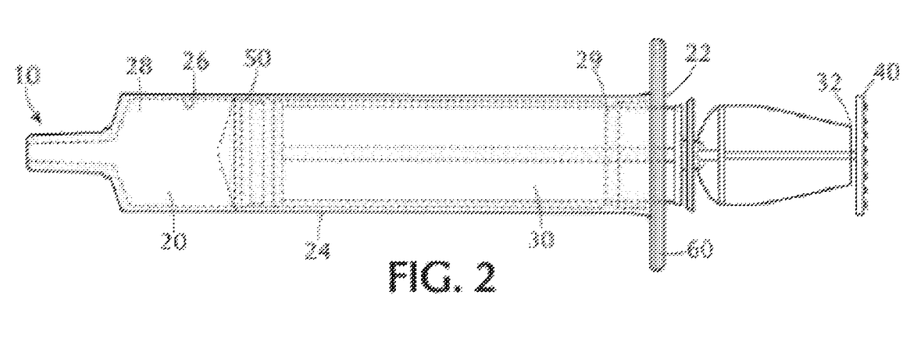
FIG. 2 shows a syringe assembly with the plunger rod of FIG. 1 being moved in the distal direction.

As shown more clearly in FIG. 1, the plunger rod 30 further includes a locking petal 70 adjacent its proximal end 32. In a specific embodiment, the locking petal can include a one or more individual petals disposed around the entire circumference of the plunger rod. In a preferred embodiment, the locking petal includes four individual petals disposed around the entire circumference of the plunger rod, as shown in FIGS. 1 and 2. In the embodiment shown in FIG. 1, the locking petal 70 includes four radially outwardly extending leaves 701, 702, 703, 704 attached to the plunger rod 30 and extend perpendicularly or radially outwardly from the plunger rod. The outer edge of the leaves 701, 702, 703, 704 may also include a tapered edge that facilitates movement of the locking petal distally past the locking element. In one or more embodiments, the force exerted by the locking element on the leaves 701, 702, 703, 704 of the locking petal 70 exceeds the force required to break the at least one frangible element 39 comprising a connection or break point at the proximal end of the plunger rod disposed either inside the thumb press or immediately adjacent to the thumb press to separate the thumb press from the main body of the plunger rod when a user applies sufficient proximal force to the plunger rod after it has been locked.

Figure 6:
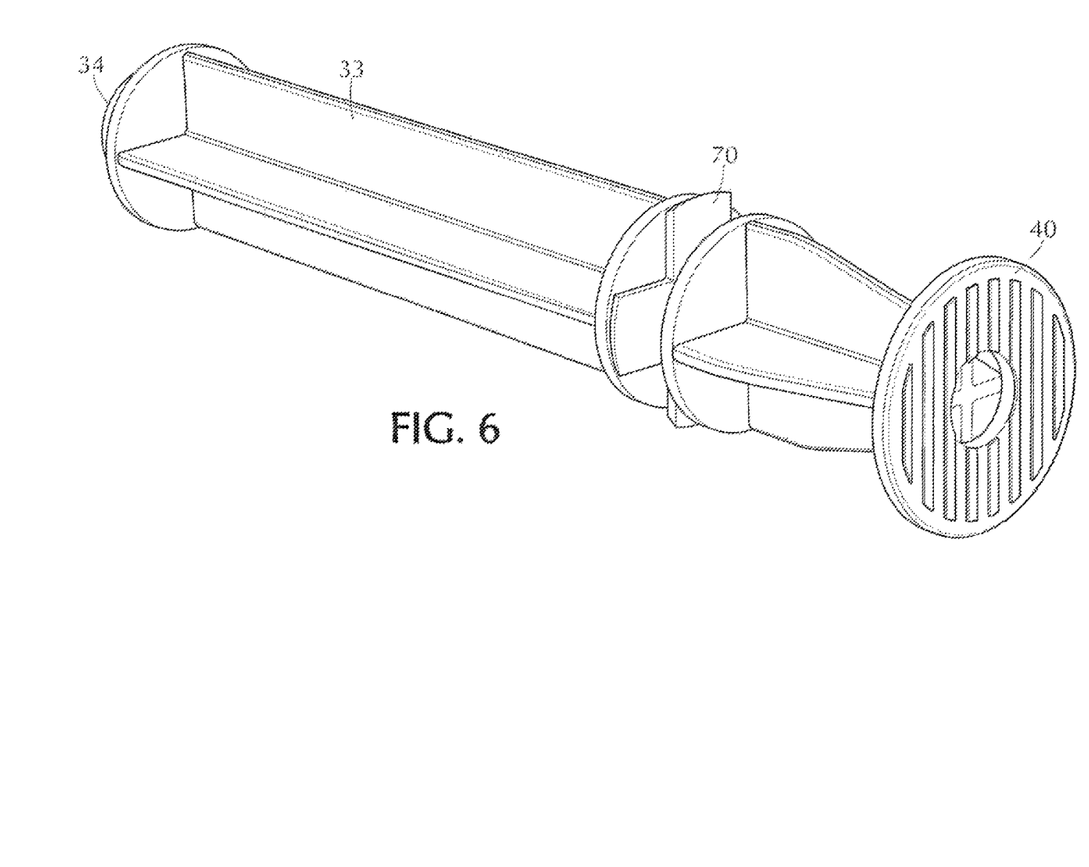
FIG. 6 shows a perspective view of one embodiment of the thumb press of FIG. 1 having a plurality of break points under the thumb press.
Figure 7:
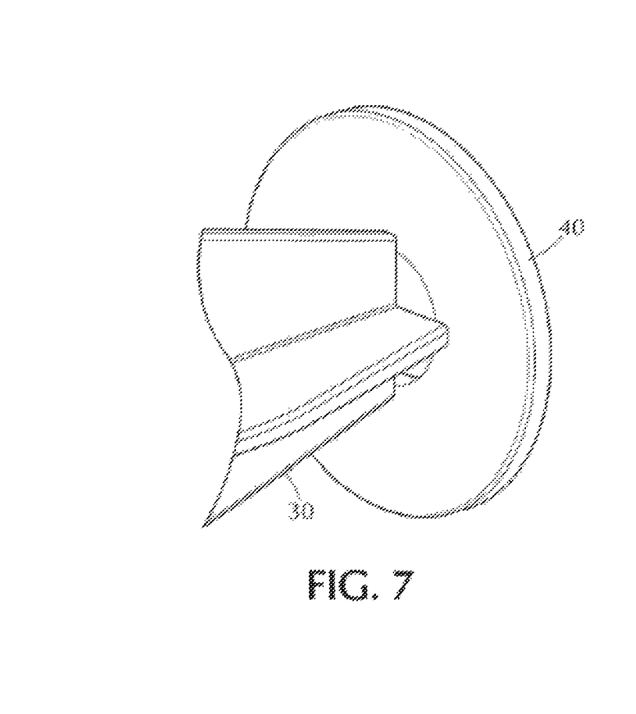
FIG. 7 shows a perspective view of one embodiment of the thumb press of FIG. 6 having a plurality of break points under the thumb press from a distal end.
Figure 8:
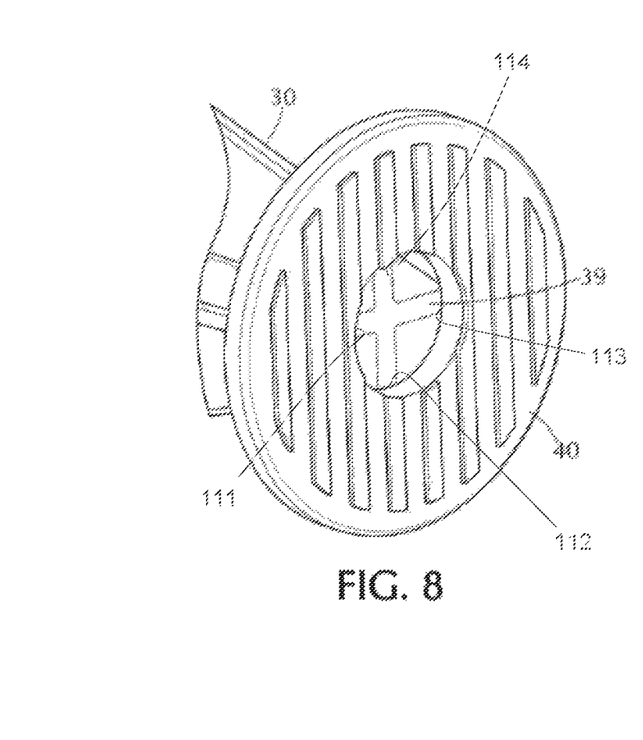
FIG. 8 shows a perspective view of one embodiment of the thumb press shown in FIG. 6 from a proximal end.
Figure 9:
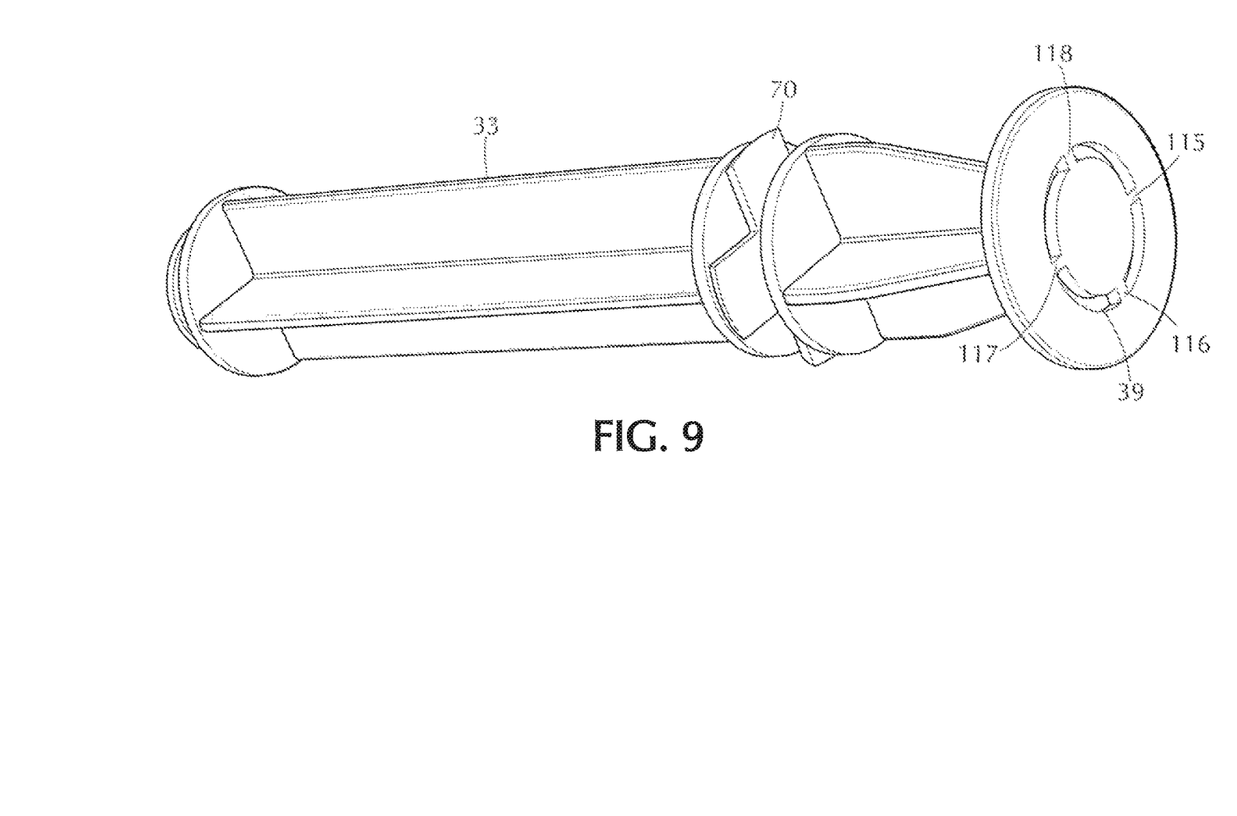
FIG. 9 shows a perspective view of one embodiment of the thumb press of FIG. 1 having a plurality of break points inside the thumb press.

The locking petal 70 of the plunger rod may also be in the form of detents or tabs can also be used to retain the plunger rod 30 in the barrel. In one or more embodiments, the outer diameter of the plunger rod at the locking petal 70 can be lesser than or greater than the inner diameter of the barrel 20 at the tapered neck portion. In some embodiments of the invention, the locking petal 70 includes a tapered portion that facilitates distal movement of the locking petal 70 past the locking element of the barrel 20, as will become apparent in the subsequent discussion of operation of the syringe. In at least one embodiment, the syringe assembly is configured to allow the locking petal 70 to advance distally past the tapered neck portion 92, to lock the plunger rod in the barrel when the user bottoms out the plunger rod in the barrel (as more clearly shown in FIG. 3). In certain embodiments, the plunger rod 30 further includes at least one frangible element 39 comprising a connection or break point at the proximal end of the plunger rod disposed either inside the thumb press or immediately adjacent to the thumb press for separating the thumb press from the main body of the plunger rod when a user applies sufficient proximal force to the plunger rod after it has been locked. In the embodiment shown, the frangible element 39 is located at the proximal end of the plunger rod disposed either immediately adjacent to the thumb press, as shown in FIGS. 1-7 or inside the thumb press, as shown in FIGS. 8-9. It will be understood that the frangible element 39 comprising a connection or break point shown is exemplary, and other suitable means for permanently damaging the plunger rod or otherwise separating at least a portion of the plunger rod from the main body may be provided.

The plunger rod may be made of plastic or other suitable material. The locking petals 70 may also be comprised of plastic or a harder material suitable for locking the plunger rod within the barrel.

As shown in FIG. 2, the syringe assembly 10 includes a barrel 20, a plunger rod 30 with thumb press 40 and a stopper 50, arranged such that the proximal end 32 of plunger rod is attached to the distal end 42 of the thumb press. Referring now to FIG. 2, the stopper 50 has a distal end, a proximal end, a stopper body and a peripheral edge which forms a seal with the interior surface 26 of the barrel. The stopper may be either integral or removably connected to the distal end of the plunger rod. The stopper is typically made of plastic or other easily disposable and/or recyclable material. It may be desirable to incorporate natural or synthetic rubber in the stopper or use a natural or synthetic rubber seal with the stopper. It will be understood that the stopper may incorporate multiple seals.

The connected thumb press 40 and plunger rod 30 are inserted into the proximal end 22 of the barrel 20.

As best shown in the FIG. 2, the barrel 20 has a cylindrical sidewall 24 with an interior surface 26 that defines a chamber 28. The sidewall 24 of the barrel may define a chamber 28 having a continuous inner diameter along the longitudinal axis of the syringe. Alternatively, the barrel 20 can include a sidewall 24 having an inner diameter, which decreases linearly from the proximal end to the distal end. It is to be understood that the configuration shown is merely exemplary, and the components can be different in shape and size than shown. In one embodiment, the chamber 28 holds the contents of the syringe assembly which may include medication in fluid form. The barrel 20 is shown as having an open proximal end 22, a distal end 23, and a distal wall 25. The distal wall 25 has an opening 27 in fluid communication with the chamber 28.

The syringe barrel 20 is shown as having a peripheral flange 60 attached at the proximal end 22 of the barrel 20. The barrel 20 may further include a needle cannula attached to the opening 27 in the distal end 23 of the barrel 20. As is known in the art, attachment means may be provided for attaching a needle cannula to the distal wall 25. The syringe assembly 10 may also include a protective cap over the needle cannula (not shown).

One or more optional tabs or detents can be used to create a region of the barrel having a diameter smaller than the inner diameter of the barrel 20. In a specific embodiment, a ring may be formed along entire circumference of the interior surface or a portion of the interior surface of the inner diameter of the barrel 20 (not shown). In one or more embodiments, the locking petals of the plunger rod have a larger diameter than the diameter of the interior surface of the barrel at the locking element.

Figure 3:
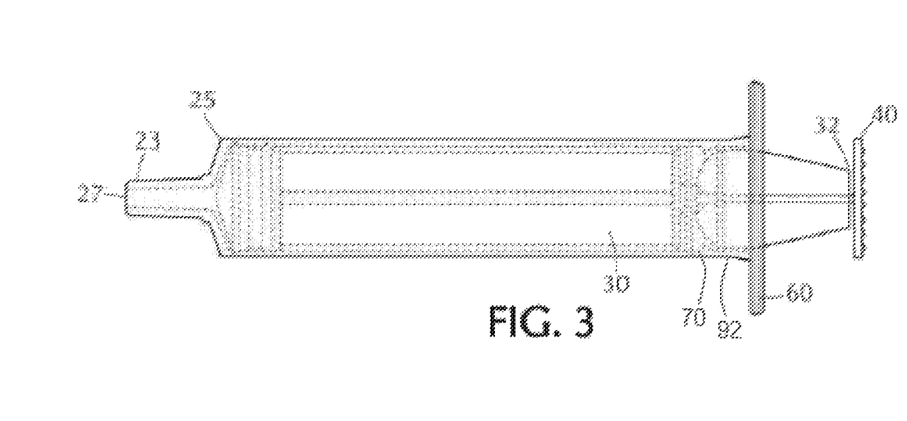
FIG. 3 shows the plunger rod of FIG. 1 in a locked position in the syringe barrel.
Figure 5:
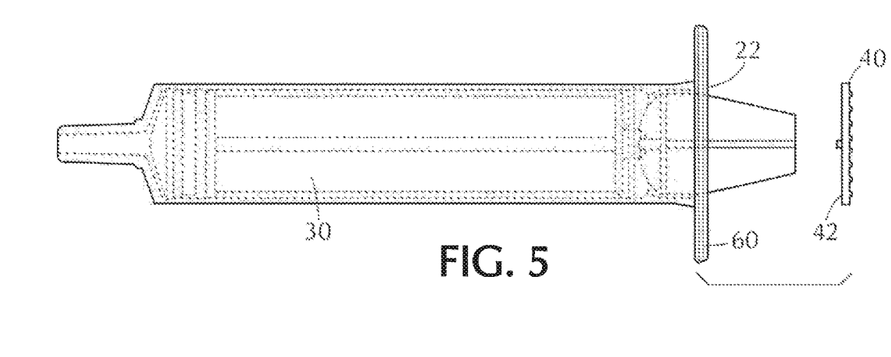
FIG. 5 shows a distal portion of the thumb press of FIG. 1 being broken from the plunger rod after the plunger rod has been locked in the syringe barrel.

In another embodiment, the barrel 20 may include a tapered diameter transition region 92 at the proximal end 22 (as shown in FIGS. 2, 3 and 5) of the barrel 20. The inner diameter of the barrel at the diameter transition region 92 decreases from the proximal end 22 towards the distal end 23 and forms a ramp/neck 29 in the barrel 20 as shown in FIGS. 2 and 3. The barrel 20 is shown as further having a tapered portion at its proximal end 22. A neck 29 is at the distal end of tapered diameter transition region 92 at the proximal end 22 (as shown in FIGS. 2, 3 and 5) of the barrel 20. The locking petal 70 is provided to help retain the plunger rod 30 in the barrel after the locking petal is pushed past the tapered portion 92 of the barrel 20. The diameter of the locking petal 70 of the plunger rod is larger than the inner diameter of the barrel at the diameter transition region 92. Specifically, the flexible locking petals 70 flex as they move past the narrowed diameter of the tapered neck portion 92 of the barrel. In one or more embodiments, as the locking petals 70 move distally past the tapered neck portion 92, a slight increase in force may be applied to the plunger rod. According to the embodiment shown, this slight increase in force applied to the plunger rod is not perceptible to a user during normal use of the syringe. Further, the ramp of the barrel facilitates movement of the flexible locking petals 70 past the tapered neck portion 92. After the flexible locking petals 70 have advanced distally past the tapered neck portion 92, the distal portion of the tapered neck portion 92 restricts movement of the flexible locking petals 70 in the proximal direction. It is believed that the break force, as defined herein, is less than the force required to withdraw the plunger rod.

In one or more alternative embodiments, the tapered neck portion 92 may have an alternative configuration, shape or size that prevents the plunger rod from being removed from the barrel 20 or to lock the plunger rod 30 within the barrel. In another embodiment, the tapered neck portion 92 is formed along the inside surface 26 of the barrel and extends to form an annular wall that projects or extends radially into the chamber 28. In other embodiments, the tapered neck portion 92 may include a single or more than one locking petals 70 (not shown) that extends into the chamber 28.

The barrel may be made of plastic, glass or other suitable material.

Figure 4:
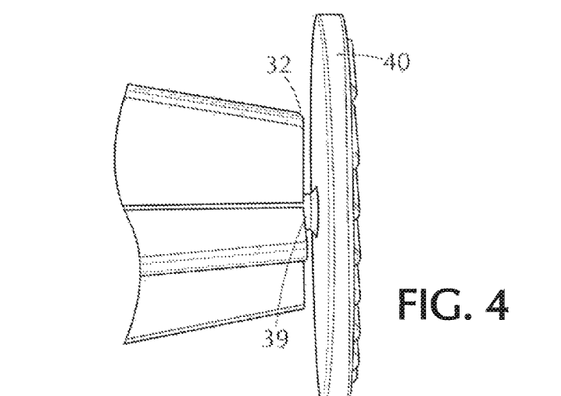
FIG. 4 shows a proximal portion of the plunger rod of FIG. 1 having a frangible element located between the thumb press and proximal end of the plunger rod.

In a preferred embodiment, the re-use prevention locking syringe contains a single frangible element 39 immediately under the thumb press 40. FIG. 4 shows the proximal portion of the plunger rod of FIG. 1 having a frangible element 39 located between the thumb press 40 and proximal end 32 of the plunger rod 30.

FIG. 2 shows a syringe assembly with the plunger rod of FIG. 1 being moved in the distal direction. As the injection is completed, the re-use prevention mechanism locks the syringe. FIG. 3 shows the plunger rod of FIG. 1 in a locked position in the syringe barrel.

If re-use of the syringe is attempted by pulling on the plunger rod to disengage the lock, the frangible section 39 under the thumb press 40 breaks and the syringe is permanently disabled. FIG. 5 shows a distal portion of the thumb press 40 of FIG. 1 being broken from the plunger rod after the plunger rod has been locked in the syringe barrel.

In one or more embodiments of the present invention, the syringe assembly includes a plurality of break points at the proximal end of the plunger rod disposed either inside the thumb press or immediately adjacent to the thumb press. The frangible element 39 may include a plurality of frangible connections or break points formed at the immediate interface of the thumb press and the proximal portion of the plunger rod as shown in FIGS. 6 and 7. FIG. 6 shows a perspective view of one embodiment of the thumb press of FIG. 1 having a plurality of break points 110 under the thumb press. FIG. 7 shows a perspective view of one embodiment of the thumb press of FIG. 6 having a plurality of break points under the thumb press from a distal end. FIG. 8 shows a perspective view of the embodiment of the thumb press shown in FIG. 6 from a proximal end. In the embodiment shown in FIG. 8, the frangible element includes four break point connections 111, 112, 113, 114 respectively disposed on the four quadrants formed by the two intersecting transverse members of the plunger rod. The break point connections 111, 112, 113, 114 are distributed such that they are dispersed across the proximally facing surface of the plunger rod to attach the plunger rod to the thumb press.

Figure 10:
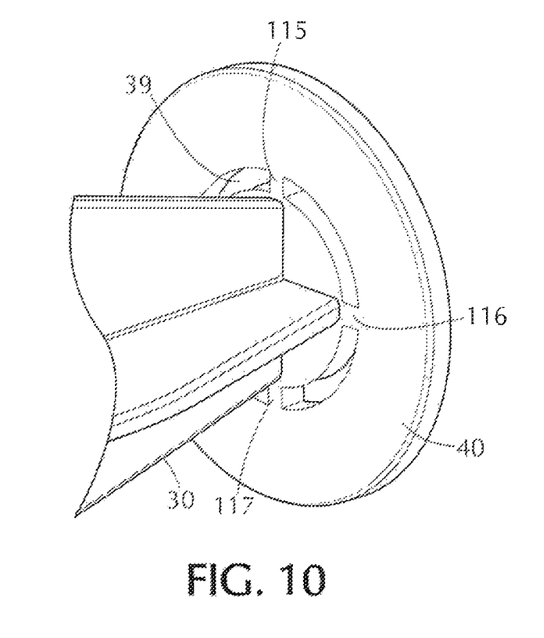
FIG. 10 shows a perspective view of one embodiment of the thumb press of FIG. 8 having a plurality of break points inside the thumb press from a distal end.
Figure 11:
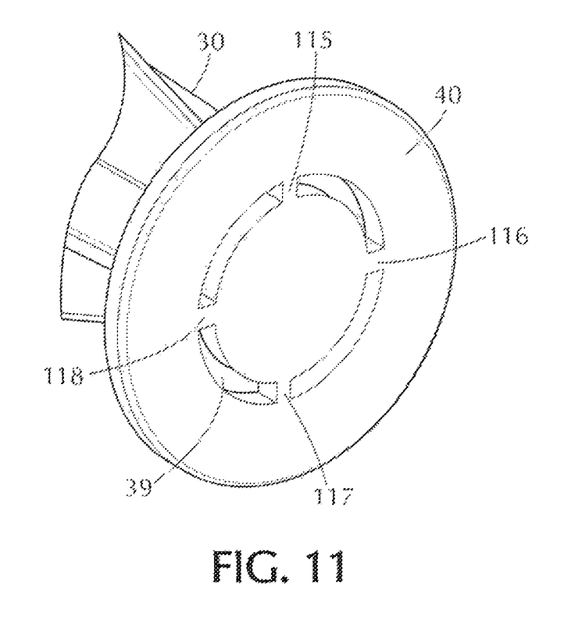
FIG. 11 shows a perspective view of another embodiment of the thumb press shown in FIG. 8 from a proximal end.

As shown in FIGS. 9-11, the thumb press may include a frangible element comprising a plurality of one or more frangible connections or break points inside the thumb press extending radially to attach to the proximal end of the plunger rod. The frangible element, as shown in FIGS. 9-11 is in the form of a knock-out tab disposed inside the thumb press and extending radially from the thumb press to the plunger rod body. As shown in FIGS. 9-11, the knock-out tab disposed inside the thumb press has four break points 115, 116, 117, 118, each break point extending radially to removably attach the thumb press to the plunger rod body. FIG. 9 shows a perspective view of one embodiment of the thumb press of FIG. 1 having a plurality of break points 115, 116, 117, 118 inside the thumb press. FIG. 10 shows a perspective view of one embodiment of the thumb press of FIG. 9 having a plurality of break points inside the thumb press from a distal end. FIG. 11 shows a perspective view of another embodiment of the thumb press shown in FIG. 9 from a proximal end.

The plurality of break point connections 115, 116, 117, 118 may be described as connecting the thumb press 40 to the proximal end 32 of the plunger rod. In the embodiment shown in FIGS. 9-11, the frangible element 39 includes four break point connections 115, 116, 117, 118. In one or more embodiments, the frangible element 39 may include one, two, three or more than four point connections (not shown). In the embodiment shown in FIGS. 9-11, the break point connections 115, 116, 117, 118 are dispersed under or inside the thumb press to provide stability the plunger rod 30 during use. The distance between the break point connections may be constant or may vary. In one or more alternative embodiments, the frangible element 39 may include other structure that permits a portion of the plunger rod 30 to separate from the thumb press 40.

Additional solutions to improving the plunger rod's rigidity is a spacer feature, such as a clip or a bump, to fill the gap around the frangible element thus reducing its range of undesired motion. The clip and thumb press interface may have protruding features to keep it engaged on the plunger rod by preventing the clip's rotation. The gap in the plunger rod around the frangible element may also be reduced by having bump features on the plunger rod that fill the gap while allowing the part to be molded. These bump features may be either molded into the part geometry or formed into the thumb press after the part is molded, by heat staking for example. The spacer feature may also be implemented on other frangible element locations, away from the thumb press, such as near the stopper end. The frangible element adjacent to the thumb press may have a plurality of break points. The frangible element may be located inside the thumb press.

Figure 12:
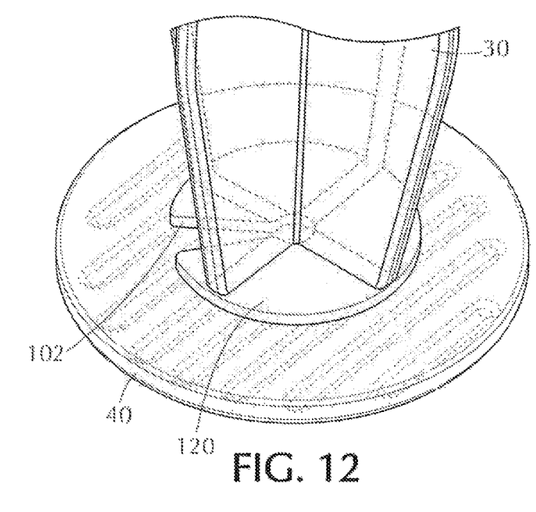
FIG. 12 shows a perspective view of a spacer clip disposed between the thumb press and plunger rod.

To restrict motion of the compliant thumb press, a flat spacer clip may be inserted into the gap around the frangible element. In one or more embodiments of the present invention, the plunger rod includes a spacer clip 120 disposed in the gap formed by the frangible element between the thumb press and the main body of the plunger rod as shown in FIG. 12. FIG. 12 shows a perspective view of a spacer clip 120 disposed between the thumb press 40 and plunger rod 30 comprising an insertion slot 102 to allow the spacer clip to be placed about the frangible element. As shown in FIG. 12, the spacer clip is disposed in a perpendicular orientation about the axis of the single break point of the frangible element. The spacer clip may be stamped or molded. The spacer clip provides additional stability to the plunger rod during use by limiting the moment arm caused by the gap formed by the single break point of the frangible element between the thumb press and the main body of the plunger rod as shown in FIG. 12. The spacer clip may have alternate shapes, depending on the shape of the plunger rod and/or barrel. The spacer clip may be made from plastic or metal or other suitable material.

Figure 13:
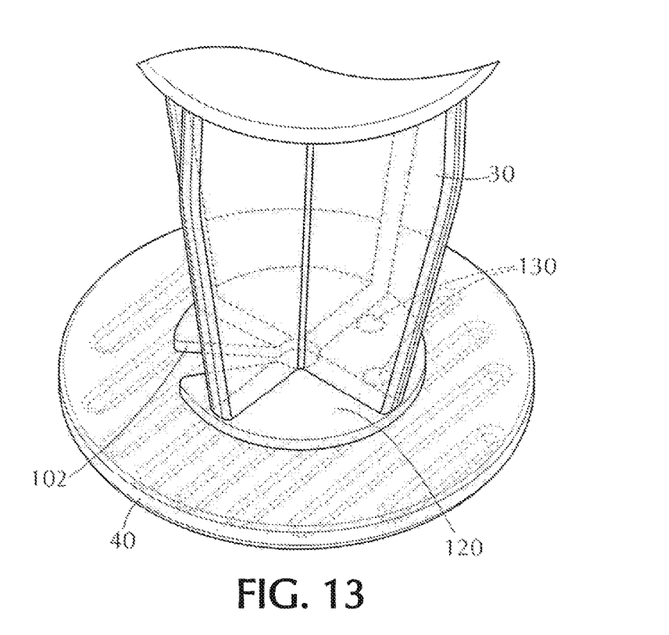
FIG. 13 shows a perspective view of another embodiment of the spacer clip shown in FIG. 10 having anti-rotation bumps.

In one or more embodiments of the present invention, the spacer clip may include two or more anti-rotation bumps disposed on the spacer clip. FIG. 13 shows a perspective view of an embodiment of the spacer clip shown in FIG. 12 having anti-rotation bumps 130. The interdigitating anti-rotation bumps prevent the spacer clip from rotation and prevent the insertion slot from aligning with any of the intersecting transverse members of the plunger rod that the clip is intended to support. As shown in FIG. 13, the interdigitating anti-rotation bumps may be disposed within one or more of the four quadrants formed by the two intersecting transverse members of the plunger rod.

Figure 14:
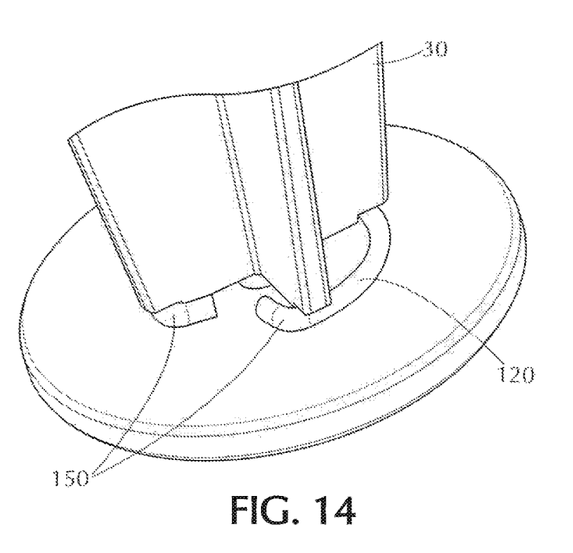
FIG. 14 shows a perspective view of a spacer clip formed from a wire and a step molded into the plunger rod to accommodate the spacer clip and register the spacer clip's retaining hooks.

In one or more embodiments of the present invention, the spacer clip is formed from a wire. In one or more embodiments of the present invention, a step is molded into the plunger rod to accommodate the spacer clip and register the spacer clip's retaining hooks 150. FIG. 14 shows a perspective view of a spacer clip formed from a wire and a step molded into the plunger rod to accommodate the spacer clip and register the spacer clip's retaining hooks.

Figure 15:
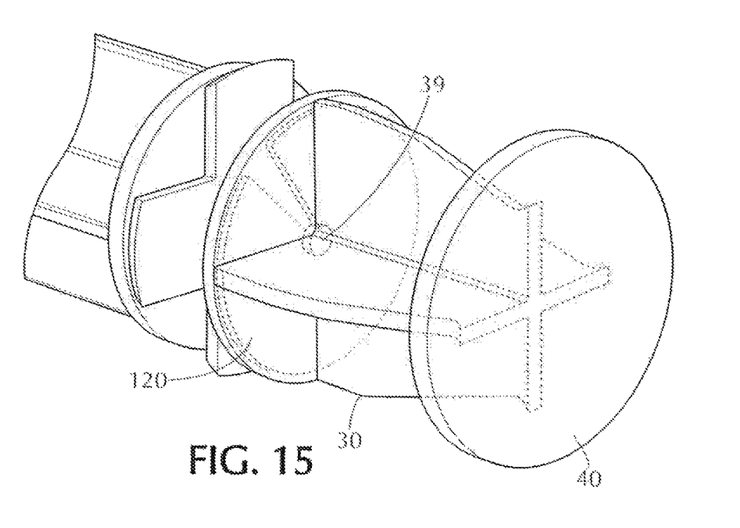
FIG. 15 shows a perspective view of a spacer clip and frangible element disposed at a distance from the thumb press.

In one or more embodiments of the present invention, the spacer clip is disposed at a distance from the thumb press. The spacer clip can be used to limit the plunger rod's flexing around a frangible element located away from the thumb press. FIG. 15 shows a perspective view of a spacer clip and frangible element disposed at a distance from the thumb press.

In one or more embodiments of the present invention, bumps may be used to fill the surrounding gap thus restricting the bending motion thereby improving the rigidity of the plunger rod around its frangible element. The bumps can be molded or heat staked into the part.

Figure 16:
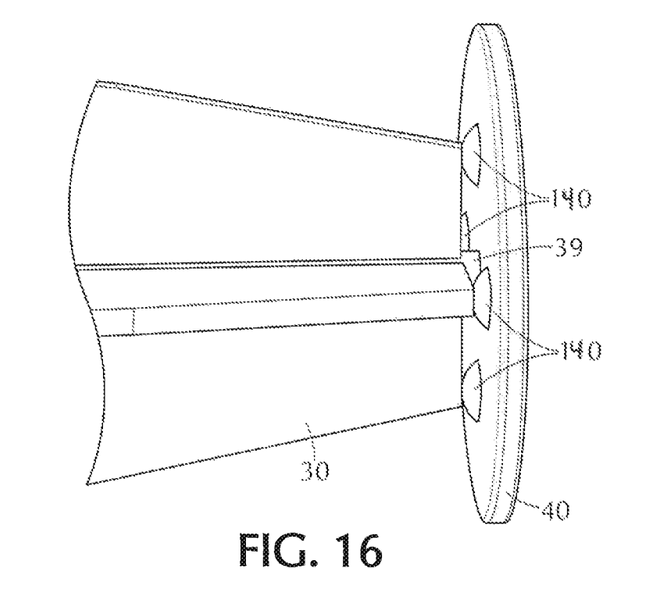
FIG. 16 shows a perspective view of another embodiment of the thumb press, plunger rod and frangible element wherein spacer bumps are disposed between the distal end of the thumb press and proximal end of the plunger rod.

FIG. 16 shows a perspective view of another embodiment of the thumb press, plunger rod and frangible element wherein spacer bumps 140 are disposed between the distal end of the thumb press and proximal end of the plunger rod. As shown in FIGS. 14 and 15, the spacer bumps 140 may be disposed between the intersection of the thumb press and one or more of the four quadrants formed by the two intersecting transverse members of the plunger rod to fill the gap caused by the single break point of the frangible element.

The frangible element comprising one or more break point under the thumb press may have some localized motion during use due to the gap required to mold the geometry. This thumb press compliance may be beneficial for a variety of devices as it may improve their tactile feel.

Use

In one embodiment, the plunger rod is permitted to move distally and proximally within the barrel until the locking petal 70 is pushed past the locking element of the barrel to lock the plunger rod in the barrel.

In another embodiment, the plunger rod is permitted to move distally and proximally within the barrel until the locking petal 70 is pushed past the tapered neck portion of the barrel to lock the plunger rod in the barrel.

As the user expels the contents of the syringe, the plunger rod and locking petals 70 move together in the distal direction, the locking petal 70 is permitted to move past the locking tapered neck portion 92 of the barrel.

In FIG. 2, the barrel 20 holds the plunger rod 30 in the chamber, wherein the stopper is bottomed, "parked" or is in contact with the distal wall 25 of the barrel 20. The peripheral edge of the stopper forms a seal with the interior surface 26 of the barrel 20. In one embodiment, the stopper 50 is connected to the stopper-engaging portion 37 of the plunger rod 30. The locking petal 70 is held in the barrel 20 by the tapered neck portion 92.

FIGS. 2, 3 and 5 show the syringe assembly according to one or more embodiments of the present invention in use and specifically demonstrates application of distal force to the plunger rod during injection. In one embodiment, when the user applies a force in the distal direction to the plunger rod 30, the plunger rod 30 moves in a distal direction. In one embodiment, the user may inject a limited amount of the fluid aspirated or exert a limited force on the plunger rod in the distal direction to flush or expel some of the aspirated fluid, without locking the plunger rod, provided that the locking petal 70 is not pushed past the tapered neck portion 92 of the barrel to lock the plunger rod into the barrel and the syringe assembly is not bottomed. However, as will be described further with respect to FIG. 3, a user may bottom the stopper against the distal wall of the syringe barrel, locking the plunger rod in the barrel by pushing the locking petal 70 past the tapered neck portion 92 of the barrel.

As more clearly shown in FIGS. 2-3, the barrel further includes a tapered neck portion 92, locking tapered neck portion 92 or other means for locking the plunger rod within the barrel, having an interior surface with a smaller diameter than the diameter of the interior surface of the barrel. The distal end of the tapered neck portion 92 further includes a distal portion facing the distal end of the barrel. It will be understood that the tapered neck portion 92 and the distal portion of the tapered neck portion 92 can have different shapes and configurations. A ramp may be disposed proximally adjacent to the tapered neck portion 92 having an increasing diameter from the tapered neck portion 92 to the open proximal end. An increased diameter region may be disposed proximally adjacent to the ramp.

FIG. 3 illustrates an embodiment of the syringe assembly after the plunger rod has been locked inside the barrel. In one or more embodiments, application of force in a distal direction allows the locking petals 70 to advance past the tapered neck portion 92 (as more clearly shown in FIG. 3), thereby locking the plunger rod inside the barrel preventing re-use of the syringe assembly. The locking petals 70 have an outer diameter greater than the inner diameter of the barrel at the tapered neck portion 92. Accordingly, in one or more embodiments, the tapered neck portion 92 locks the locking petals 70 inside the barrel 20, and prevents proximal movement of the plunger rod 30.

FIG. 3 shows the assembly after the plunger rod 30 has been locked in the barrel 20. An attempt to reuse the syringe assembly by applying a force to the plunger rod 30 in the proximal direction causes the thumb press to separate from the plunger rod 30 at the frangible element 39 comprising one or more frangible connections or break points located at the proximal end of the plunger rod disposed either immediately adjacent to the thumb press, as shown in FIGS. 1-7 or inside the thumb press, as shown in FIGS. 8-9. The frangible element 39 comprising one or more frangible connections or break points is designed so that the force holding exerted on the locking petals 70 by the locking tapered neck portion 92 while proximal force is being applied to the plunger rod 30 is greater than the force needed to break the thumb press from the plunger rod at the frangible point 143 and, therefore, the frangible point breaks or separates the thumb press before the user is able to overcome the force exerted on the locking petal 70 by the tapered neck portion 92.

FIG. 5 shows the syringe assembly in a configuration in which the thumb press has separated from the plunger rod. According to one or more embodiments of the invention, the thumb press and plunger rod disengage to prevent a user from disassembling the parts of the syringe assembly after use. When a user applies a force to the plunger rod 30 in the proximal direction, the tapered neck portion 92 locks the peripheral edge of the locking petals 70.

Application of sufficient proximal force to the plunger rod causes the thumb press to separate from the proximal end 32 of the plunger rod at the frangible element 39 comprising one or more frangible connections or break points, as the holding force of the tapered neck portion 92 on locking petals 70 exceeds the breaking force of the one or more frangible break points or connections.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A syringe assembly comprising:
 a barrel including a cylindrical sidewall having an interior surface with a first cross-sectional width defining a chamber for retaining fluid, an open proximal end and a distal end including a distal wall having an opening therethrough in fluid communication with said chamber;
 an elongate plunger rod including a proximal end and a distal end, a main body of the plunger rod extending between the proximal end of the plunger rod and the distal end of the plunger rod;

a thumb press comprising a radial disc;
a single, circular frangible element disposed at an immediate interface of the thumb press and the proximal end of the plunger rod, the frangible element comprising one break point connection immediately under the thumb press having a gap extending radially from the frangible element, the gap having a uniform width between the thumb press and the proximal end of the plunger rod, the one break point connection of the frangible element connects the thumb press to the proximal end of the plunger rod, the one break point connection adapted to provide a minimum moment arm from the thumb press to the one break point connection of the frangible element;
a removable spacer clip disposed in the gap around the frangible element between the thumb press and the proximal end of the plunger rod;
the plunger rod being distally and proximally movable within the chamber, the distal end including a stopper slidably positioned in fluid-tight engagement with the inside surface of the barrel for drawing fluid into and driving fluid out of the chamber by movement of the stopper relative to the barrel;
a locking element disposed on one or more of the barrel and plunger rod wherein the locking element comprises a flexible locking petal between the thumb press and the main body, and the flexible locking petal includes four individual leaves disposed around an entire circumference of the plunger rod;
a ramp disposed proximally adjacent to the locking element having an increasing diameter from the locking element to the open proximal end; and
wherein application of a continuous distally directed force to the plunger rod causes the stopper and plunger rod to move together in the distal direction within the barrel past the ramp until the locking element locks the plunger rod in the barrel, the frangible element being located outside of the barrel when the plunger rod is locked within the barrel by the locking element.

2. The syringe assembly of claim 1, wherein a subsequent application of a proximally directed force to the plunger causes the frangible element of the plunger rod to break and separates the thumb press from the main body of the plunger rod to prevent reuse of the syringe assembly.

3. The syringe assembly of claim 1, wherein the one break point connection is adapted to withstand application of a force on the plunger rod in the distal direction and break upon application of a force in the proximal direction after the locking element locks the plunger rod in the barrel.

4. The syringe assembly of claim 1, wherein a force required to move the plunger rod in a proximal direction after the locking element locks the plunger rod in the barrel exceeds a force required to break the one break point connection.

5. The syringe assembly of claim 1, wherein the frangible element is disposed at the proximal end of the plunger rod immediately under the distal end of the thumb press.

6. The syringe assembly of claim 1, wherein the individual leaves include a tapered outer edge.

7. The syringe assembly of claim 1, wherein the locking petal is permitted to advance distally past the ramp and a locking element disposed in the sidewall of the barrel and lock the plunger rod in the barrel to prevent reuse of the syringe assembly.

8. The syringe assembly of claim 1, wherein the locking element is disposed on the barrel and comprises a second cross-sectional width that is less than a first cross-sectional width of the barrel.

9. The syringe assembly of claim 1, further comprising one or more spacer bumps disposed between the distal end of the thumb press and proximal end of the plunger rod.

10. The syringe assembly of claim 1, wherein the removable spacer clip is disposed in the gap around the frangible element between the thumb press and the proximal end of the plunger rod at a perpendicular orientation to the frangible element.

11. The syringe assembly of claim 10, wherein the spacer clip and frangible element are disposed at a distance from the thumb press.

12. The syringe assembly of claim 1, wherein the spacer clip comprises one or more anti-rotation bumps.

13. The syringe assembly of claim 1, wherein the spacer clip comprises one or more retaining hooks.

* * * * *